US012806085B2

(12) United States Patent
Garcia et al.

(10) Patent No.: US 12,806,085 B2
(45) Date of Patent: Nov. 24, 2026

(54) TEXTILE BACKSHEET

(71) Applicant: Berry Global, Inc., Evansville, IN (US)

(72) Inventors: Robert Garcia, Alcanar (ES); Kay Alsleben, Aschersleben (DE); Frank Eschenbacher, Schnelldorf (DE); Jozef Van Kerrebrouck, Wingene (BE)

(73) Assignee: MAGNERA CORPORATION, Charlotte, NC (US)

( * ) Notice: Subject to any disclaimer, the term of this patent is extended or adjusted under 35 U.S.C. 154(b) by 577 days.

(21) Appl. No.: 17/951,668

(22) Filed: Sep. 23, 2022

(65) Prior Publication Data

US 2023/0025746 A1 Jan. 26, 2023

Related U.S. Application Data

(63) Continuation-in-part of application No. 17/825,037, filed on May 26, 2022.

(60) Provisional application No. 63/194,348, filed on May 28, 2021.

(51) Int. Cl.

*B32B 5/26* (2006.01)
*A61F 13/514* (2006.01)
*B32B 5/02* (2006.01)

(52) U.S. Cl.

CPC ............ *A61F 13/514* (2013.01); *B32B 5/022* (2013.01); *B32B 5/265* (2021.05); *B32B 2555/02* (2013.01)

(58) Field of Classification Search

CPC .. A61F 13/514; A61F 13/51401; B32B 5/022; B32B 5/265; B32B 27/32; B32B 2262/0253; B32B 2274/00; B32B 2262/16; B32B 27/12; B32B 27/285; B32B 2307/7265; B32B 27/36; B32B 27/40; B32B 2555/02

See application file for complete search history.

(56) References Cited

U.S. PATENT DOCUMENTS

| | | | | |
|---|---|---|---|---|
| 4,713,069 | A | 12/1987 | Wang et al. | |
| 4,789,699 | A | 12/1988 | Kieffer et al. | |
| 5,169,712 | A | 12/1992 | Tapp | |
| 5,208,098 | A | 5/1993 | Stover | |
| 5,409,761 | A * | 4/1995 | Langley | B32B 27/32 428/315.7 |
| 5,498,463 | A | 3/1996 | McDowall et al. | |
| 5,843,064 | A | 12/1998 | Koczab | |

(Continued)

FOREIGN PATENT DOCUMENTS

| | | | |
|---|---|---|---|
| CN | 1270555 | A | 10/2000 |
| CN | 1283978 | A | 2/2001 |

(Continued)

OTHER PUBLICATIONS

U.S. Appl. No. 63/164,687, which is a priority document that supports US 2022/0304869 (filed 2021).*

(Continued)

*Primary Examiner* — Susan S Su
(74) *Attorney, Agent, or Firm* — BURR & FORMAN

(57) ABSTRACT

Textile backsheets including a nonwoven fabric and film, such as a vapor-permeable and liquid impermeable (VPLI) film or a non-permeable film, are provided, wherein the nonwoven fabric is directly or indirectly bonded to the film. Methods of making such textile backsheets and absorbent articles including the textile backsheets are also provided.

24 Claims, 4 Drawing Sheets

(56) References Cited

U.S. PATENT DOCUMENTS

| | | | | |
|---|---|---|---|---|
| 5,938,648 | A | 8/1999 | LaVon et al. | |
| 6,045,900 | A | 4/2000 | Haffner et al. | |
| 6,916,969 | B1 | 7/2005 | Helmfridsson | |
| 12,012,352 | B2 | 6/2024 | Faynot | |
| 2002/0071944 | A1 | 6/2002 | Hugh et al. | |
| 2002/0107295 | A1* | 8/2002 | Edmundson | C08L 101/00 521/50 |
| 2004/0224136 | A1* | 11/2004 | Collier, IV | B32B 5/26 428/196 |
| 2005/0043460 | A1 | 2/2005 | McCormack et al. | |
| 2007/0287348 | A1* | 12/2007 | Autran | A61F 13/51464 442/361 |
| 2010/0249741 | A1 | 9/2010 | Fingal | |
| 2011/0112500 | A1* | 5/2011 | Wenzel | A61F 13/49011 156/227 |
| 2013/0237938 | A1* | 9/2013 | Autran | A61F 13/51464 604/365 |
| 2015/0308039 | A1* | 10/2015 | Bonaboglia | B32B 27/12 428/219 |
| 2016/0251788 | A1 | 9/2016 | Huang et al. | |
| 2017/0035625 | A1* | 2/2017 | LaVon | A61F 13/55105 |
| 2018/0168874 | A1* | 6/2018 | LaVon | A61F 13/4902 |
| 2019/0001638 | A1 | 1/2019 | Zhao et al. | |
| 2019/0136426 | A1* | 5/2019 | Hansen | D04H 1/43832 |
| 2022/0304869 | A1* | 9/2022 | Arizti | A61F 13/5633 |
| 2022/0378631 | A1 | 12/2022 | Garcia et al. | |

FOREIGN PATENT DOCUMENTS

| | | | |
|---|---|---|---|
| CN | 105121150 | A | 12/2015 |
| CN | 107106347 | A | 8/2017 |
| CN | 107107544 | A | 8/2017 |
| CN | 110831756 | A | 2/2020 |
| EP | 2732963 | A1 | 5/2014 |
| EP | 3538046 | B1 | 12/2020 |
| GB | 2290052 | A | 12/1995 |
| JP | 2002521241 | A | 7/2002 |
| JP | 2019528383 | A | 10/2019 |
| JP | 2020527978 | A1 | 9/2020 |
| WO | 1996016562 | A1 | 6/1996 |
| WO | 1997048358 | A1 | 12/1997 |
| WO | 1998002610 | A1 | 1/1998 |
| WO | 1999054134 | A1 | 10/1999 |
| WO | 2020152863 | A1 | 7/2020 |

OTHER PUBLICATIONS

International Search Report and Written Opinion of corresponding international application No. PCT/US2022/031006 mailed on Sep. 14, 2022, all enclosed pages cited.

Second Written Opinion of corresponding international application No. PCT/US2022/031006 mailed on Apr. 13, 2023, all enclosed pages cited.

International Preliminary Report on Patentability of corresponding international application No. PCT/US2022/031006 mailed on Aug. 16, 2023, all enclosed pages cited.

International Search Report and Written Opinion of corresponding international application No. PCT/ US2023/024546 mailed on Oct. 9, 2023, all enclosed pages cited.

Intention to Grant issued in corresponding European Patent Application No. 22731936.5 mailed Jan. 10, 2025, all pages cited in its entirety.

Final Rejection issued in corresponding U.S. Appl. No. 17/825,037 mailed Jan. 27, 2025, all pages cited in its entirety.

Extended Search Report and Written Opinion from the corresponding European Application No. 25180414.2, mailed Aug. 19, 2025, all pages cited in its entirety.

Final Office Action from the corresponding U.S. Appl. No. 17/825,037, mailed Aug. 11, 2025, all pages cited in its entirety.

Intention to Grant from corresponding European Application No. 23739706.2, mailed Sep. 23, 2025, all pages cited in its entirety.

Final Office Action from corresponding U.S. Appl. No. 17/825,037, mailed Jan. 23, 2026, all pages cited in its entirety.

Notice of Reasons for Refusal from corresponding Japanese Application No. 2023-573233, mailed Jan. 19, 2026, all pages cited in its entirety.

Non-Final Office Action from corresponding U.S. Appl. No. 17/825,037, mailed May 11, 2025, all pages cited in its entirety.

Notification of the First Office Action from corresponding Chinese Application No. 202280038456.X, mailed Apr. 29, 2026, all pages cited in its entirety.

Extended Search Report and Written Opinion from corresponding European Application No. 26153297, mailed May 29, 2026, all pages cited in its entirety.

Communication Pursuant to Article 94(3) from corresponding European Application No. 25180414.2, Jul. 1, 2026, all pages cited in its entirety.

Final Office Action from corresponding U.S. Appl. No. 17/825,037, mailed Oct. 1, 2026, all pages cited in its entirety.

Notice of Reasons for Refusal from corresponding Japanese Application No. 2023-573233, mailed Aug. 18, 2026, all pages cited in its entirety.

* cited by examiner

TEXTILE BACKSHEET

CROSS-REFERENCE TO RELATED APPLICATIONS

This application is a continuation-in-part and claims priority to and the benefit of prior-filed co-pending U.S. application Ser. No. 17/825,037 filed on May 26, 2022, which claims priority under 35 U.S.C. § 119 to U.S. Patent Application No. 63/194,348 filed May 28, 2021, is the contents of each are expressly incorporated by reference herein in their entirety.

TECHNICAL FIELD

Embodiments of the presently-disclosed invention relate generally to textile backsheets (TBS) including a nonwoven fabric and a film, such as a vapor-permeable and liquid impermeable (VPLI) film or a non-permeable film, in which the nonwoven fabric is directly or indirectly bonded to the film. Embodiments of the presently-disclosed invention also relate to methods of forming such a TBS, and absorbent articles including such a TBS.

BACKGROUND

Conventional absorbent articles, such as disposable diapers, employ absorbent materials located generally between a liquid pervious topsheet and a liquid impermeable backsheet to absorb body exudates. Such conventional absorbent articles have typically included elasticized waistbands and leg cuffs to help reduce the leakage of body exudates. Some conventional absorbent articles have also included elasticized containment or barrier flaps at the leg or waist sections of the article to further reduce leaks.

The liquid impermeable backsheet on conventional absorbent articles is configured to provide a barrier between the absorbent body within the absorbent article and the wearer's clothes. Typical backsheets have been both liquid and vapor impermeable. For example, many conventional absorbent articles have included a backsheet made from a polymeric film which is both liquid and vapor impermeable. To provide such backsheets with a more cloth-like feel, facing layers of nonwoven materials have been added to the polymeric film layer to provide a more pleasing feel. Unfortunately, the use of facing layers of nonwoven materials having a sufficiently soft or cloth-like feel often produce an undesirable level of lint during use by a wearer. Such linting from the nonwoven layers can lead to the onset of diaper rash.

Therefore, there remains a need in the art for textile backsheets suitable, for example, for hygiene-related applications (e.g., diapers) that provide a soft feel to a user while also providing a reduced lint formation during use by a wearer, particularly at a relatively low basis weight.

SUMMARY OF INVENTION

One or more embodiments of the invention may address one or more of the aforementioned problems. Certain embodiments according to the invention provide a textile backsheet (TBS) including a nonwoven fabric and a film, such as a vapor-permeable and liquid impermeable (VPLI) film or a non-permeable film, wherein the film has a total basis weight from about 3 to about 12 grams-per-square-meter (gsm), and wherein the nonwoven fabric is directly or indirectly bonded to the VPLI film. In accordance with certain embodiments of the invention, the TBS has (a) a basis weight from about 10 to about 20 gsm, such as at least about any of the following: 10, 11, 12, 13, 14, and 15, and/or at most about any of the following: 20, 19, 18, 17, 16, and 15 gsm, and/or (b) an abrasion resistance grade ("Grade") of at least about 3.0 as determined by SS-EN ISO 12945-2, such as at most about any of the following: 5, 4.9, 4.8, 4.7, 4.6, 4.5, 4.4, 4.3, 4.2, 4.1, and 4 as determined by SS-EN ISO 12945-2, and/or at least about any of the following: 3, 3.2, 3.4, 3.5, 3.6, 3.8, and 4 as determined by SS-EN ISO 12945-2.

In another aspect, the present invention provides an absorbent article (e.g., a diaper) including a TBS, such as a TBS disclosed herein. In accordance with certain embodiments of the invention, the absorbent article comprises a TBS, such as a TBS disclosed herein, a liquid permeable topsheet, and an absorbent body located between the TBS and the liquid permeable topsheet.

In yet another aspect, the present invention provide a method of forming a TBS, such as a TBS disclosed herein. The method may comprise providing or forming a nonwoven fabric, providing for forming a film having a total basis weight from about 3 to about 12 grams-per-square-meter (gsm), such as a VPLI film or a non-permeable film, and directly or indirectly bonding the nonwoven fabric to the film.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout, and wherein.

DETAILED DESCRIPTION

Figure 1A:
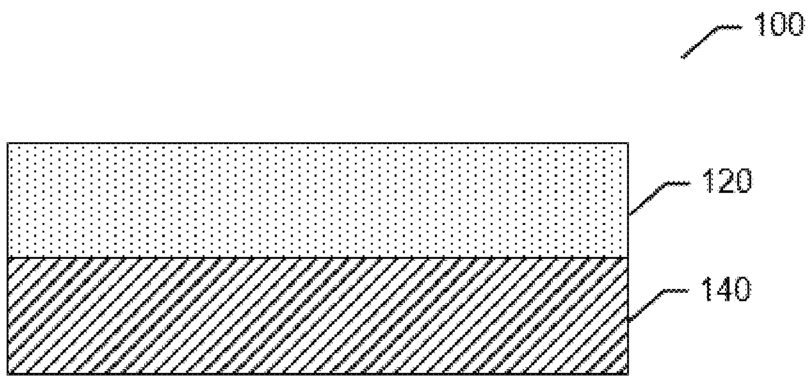
FIG. 1A illustrates a TBS including a nonwoven fabric directly bonded to a film, such as a VPLI film or a non-permeable film in accordance with certain embodiments of the invention.

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The presently-disclosed invention relates generally to textile backing sheets (TBSs) including a nonwoven fabric that is directly or indirectly attached (e.g., bonded) to a film, such as a vapor-permeable and liquid impermeable (VPLI) film or a non-permeable film. In this regard, a non-permeable film may comprise a film that is not permeable to both vapors (e.g., water vapor) and liquids. The TBSs, in accordance with certain embodiments of the invention may provide a variety of desirable properties despite utilizing a reduced amount of materials, such as a generally reduced basis weight for both the nonwoven fabric and the film, such as a VPLI film or a non-permeable film compared to traditional TBSs. For example, TBSs in accordance with certain embodiments of the invention may include an increased tensile strength per basis weight at a given bonded area, increased flexibility, and improved abrasion resistance per basis weight at a given bonded area. In accordance with certain embodiments of the invention, the TBSs may be particularly suitable for use in a variety of hygiene-related articles. Non-limiting examples of hygiene-related articles comprising a TBS in accordance with certain embodiment of the invention include femcare pads (e.g., absorbent pads), absorbent liners (e.g., panty liners), baby diapers, adult diapers, pull-ups (e.g., training pants for toddlers).

The terms "substantial" or "substantially" may encompass the whole amount as specified, according to certain embodiments of the invention, or largely but not the whole amount specified (e.g., 95%, 96%, 97%, 98%, or 99% of the whole amount specified) according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantionmers; and/or any chiral molecular configuration of such polymer or polymeric material. These configurations include, but are not limited to, isotactic, syndiotactic, and atactic configurations of such polymer or polymeric material. The term "polymer" or "polymeric" shall also include polymers made from various catalyst systems including, without limitation, the Ziegler-Natta catalyst system and the metallocene/single-site catalyst system. The term "polymer" or "polymeric" shall also include, in according to certain embodiments of the invention, polymers produced by fermentation process or biosourced.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, needle-punching, hydroentangling, air-laid, and bonded carded web processes. A "nonwoven web", as used herein, may comprise a plurality of individual fibers that have not been subjected to a consolidating process. In certain instances, the "nonwoven web" may comprises a plurality of layers, such as one or more spunbond layers and/or one or more meltblown layers. For instance, a "nonwoven web" may comprises a spunbond-meltblown-spunbond structure.

The terms "fabric" and "nonwoven fabric", as used herein, may comprise a web of fibers in which a plurality of the fibers are mechanically entangled or interconnected, fused together, and/or chemically bonded together. For example, a nonwoven web of individually laid fibers may be subjected to a bonding or consolidation process to bond at least a portion of the individually fibers together to form a coherent (e.g., united) web of interconnected fibers.

The term "consolidated" and "consolidation", as used herein, may comprise the bringing together of at least a portion of the fibers of a nonwoven web into closer proximity or attachment there-between (e.g., thermally fused together, chemically bonded together, and/or mechanically entangled together) to form a bonding site, or bonding sites, which function to increase the resistance to external forces (e.g., abrasion and tensile forces), as compared to the unconsolidated web. The bonding site or bonding sites, for example, may comprise a discrete or localized region of the web material that has been softened or melted and optionally subsequently or simultaneously compressed to form a discrete or localized deformation in the web material. Furthermore, the term "consolidated" may comprise an entire nonwoven web that has been processed such that at least a portion of the fibers are brought into closer proximity or attachment there-between (e.g., thermally fused together, chemically bonded together, and/or mechanically entangled together), such as by thermal bonding or mechanical entanglement (e.g., hydroentanglement) as merely a few examples. Such a web may be considered a "consolidated nonwoven", "nonwoven fabric" or simply as a "fabric" according to certain embodiments of the invention.

The term "staple fiber", as used herein, may comprise a cut fiber from a filament. In accordance with certain embodiments, any type of filament material may be used to form staple fibers. For example, staple fibers may be formed from polymeric fibers, and/or elastomeric fibers. Non-limiting examples of materials may comprise polyolefins (e.g., a polypropylene or polypropylene-containing copolymer), polyethylene terephthalate, and polyamides. The average length of staple fibers may comprise, by way of example only, from about 2 centimeter to about 15 centimeter.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous as disclosed and described herein. It is noted that the spunbond used in certain composites of the invention may include a nonwoven described in the literature as SPINLACE®. Spunbond fibers, for example, comprise continuous fibers.

As used herein, the term "continuous fibers" refers to fibers which are not cut from their original length prior to being formed into a nonwoven web or nonwoven fabric. Continuous fibers may have average lengths ranging from greater than about 15 centimeters to more than one meter, and up to the length of the web or fabric being formed. For example, a continuous fiber, as used herein, may comprise a fiber in which the length of the fiber is at least 1,000 times larger than the average diameter of the fiber, such as the length of the fiber being at least about 5,000, 10,000, 50,000, or 100,000 times larger than the average diameter of the fiber.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers may comprise microfibers which may be continuous or discontinuous and are generally tacky when deposited onto a collecting surface. Meltblown fibers, however, are shorter in length than those of spunbond fibers.

The term "layer", as used herein, may comprise a generally recognizable combination of similar material types and/or functions existing in the X-Y plane.

The term "multi-component fibers", as used herein, may comprise fibers formed from at least two different polymeric materials or compositions (e.g., two or more) extruded from separate extruders but spun together to form one fiber. The term "bi-component fibers", as used herein, may comprise fibers formed from two different polymeric materials or compositions extruded from separate extruders but spun together to form one fiber. The polymeric materials or polymers are arranged in a substantially constant position in distinct zones across the cross-section of the multi-component fibers and extend continuously along the length of the multi-component fibers. The configuration of such a multi-component fiber may be, for example, a sheath/core arrangement wherein one polymer is surrounded by another, an eccentric sheath/core arrangement, a side-by-side arrangement, a pie arrangement, or an "islands-in-the-sea" arrangement, each as is known in the art of multicomponent, including bicomponent, fibers.

The term "machine direction" or "MD", as used herein, comprises the direction in which the fabric produced or conveyed. The term "cross-direction" or "CD", as used herein, comprises the direction of the fabric substantially perpendicular to the MD.

The term "high-loft", as used herein, comprises a material that comprises a z-direction thickness generally in excess of about 0.3 mm and a relatively low bulk density. The thickness of a "high-loft" nonwoven and/or layer may be greater than 0.3 mm (e.g., greater than 0.4 mm. greater than 0.5 mm, or greater than 1 mm) as determined utilizing a ProGage Thickness tester (model 89-2009) available from Thwig-Albert Instrument Co. (West Berlin, New Jersey 08091), which utilizes a 2" diameter foot, having a force application of 1.45 kPa during measurement. In accordance with certain embodiments of the invention, the thickness of a "high-loft" nonwoven and/or layer may be at most about any of the following: 3, 2.75, 2.5, 2.25, 2, 1.75, 1.5, 1.25, 1.0, 0.75, and 0.5 mm and/or at least about any of the following: 0.3, 0.4, 0.5, 0.75, 1.0, 1.25, 1.5, 1.75, and 2.0 mm. "High-loft" nonwovens and/or layers, as used herein, may additionally have a relatively low density (e.g., bulk density—weight per unit volume), such as less than about 70 kg/m$^3$, such as at most about any of the following: 70, 60, 55, 50, 45, 40, 35, 30, and 25 kg/m3 and/or at least about any of the following: 10, 15, 20, 25, 30, 35, 40, 45, 50, and 55 kg/m$^3$.

The term "crimp" or "crimped", as used herein, comprises a three-dimensional curl or bend such as, for example, a folded or compressed portion having an "L" configuration, a wave portion having a "zig-zag" configuration, or a curl portion such as a helical configuration. In accordance with certain embodiments of the invention, the term "crimp" or "crimped" does not include random two-dimensional waves or undulations in a fiber, such as those associated with normal lay-down of fibers in a melt-spinning process.

As used herein, the term "aspect ratio", comprise a ratio of the length of the major axis to the length of the minor axis of the cross-section of the fiber in question.

As used herein, the term "monolithic" film may comprise any film that is continuous and substantially free or free of pores (e.g., devoid of pores). In certain alternative embodiments of the invention, a "monolithic" film may comprise fewer pore structures than would otherwise be found in a microporous film. According to certain non-limiting exemplary embodiments of the invention, a monolithic film may act as a barrier to liquids and particulate matter but allow water vapor to pass through, such as by absorbing water vapor on one side of the film, transporting the water vapor through the film, and releasing the water vapor on the opposite side of the film. In addition, without intending to be bound by theory, by achieving and maintaining high breathability, it is possible to provide an article that is more comfortable to wear because the migration of water vapor through the laminate helps reduce and/or limit discomfort resulting from excess moisture trapped against the skin. Monolithic films, according to certain embodiments of the invention, may also act as barriers to bacteria and viruses and may provide an article or garment that reduces the contamination of the surroundings and the spread of infections and illness caused by the bacteria and viruses.

The term "highly breathable polymer", as used herein, may comprise any polymer or elastomer that is selectively permeable to water vapor but substantially impermeable to liquid water and that can form a breathable film, for example, in which the polymer is capable of absorbing and desorbing water vapor and providing a barrier to aqueous fluids (e.g., water, blood, etc.). For example, a highly breathable polymer can absorb water vapor from one side of a film and release it to the other side of film, thereby allowing the water vapor to be transported through the film. As the highly breathable polymer can impart breathability to films, films formed from such polymers do not need to include pores (e.g., monolithic film). According to certain embodiments of the invention, "highly breathable polymer" may comprise any thermoplastic polymer or elastomer having a moisture vapor transmission rate (MVTR) of at least 500 g/m$^2$/day when formed into a film. According to certain embodiments of the invention, "highly breathable polymer" may comprise any thermoplastic polymer or elastomer having a MVTR of at least 750 g/m$^2$/day or of at least 1000 g/m$^2$/day when formed into a film, such as a film having, for example, a thickness of about 25 microns or less. According to certain embodiments of the invention, highly breathable polymers may comprise, for example, any one or combination of a polyether block amide copolymer (e.g., PEBAX® from Arkema Group), polyester block amide copolymer, copolyester thermoplastic elastomer (e.g., ARNITEL® from DSM Engineering Plastics, HYTREL® from E.I. DuPont de Nemours and Company), or thermoplastic urethane elastomer (TPU).

Whenever a melt flow rate (MFR) is referenced herein, the value of the MFR is determined in accordance with standard procedure ASTM D1238 (2.16 kg at 230° C.).

Certain embodiments according to the invention provide a textile backsheet (TBS) including a nonwoven fabric and a vapor-permeable and liquid impermeable (VPLI) film, wherein the nonwoven fabric is directly or indirectly bonded to the VPLI film. In accordance with certain embodiments of the invention, the TBS has (a) a basis weight from about 10 grams-per-square-meter (gsm) to about 20 gsm, such as at least about any of the following: 10, 11, 12, 13, 14, and 15, and/or at most about any of the following: 20, 19, 18, 17, 16, and 15 gsm, and/or (b) an abrasion resistance grade ("Grade") of at least about 3.0 as determined by SS-EN ISO 12945-2, such as at most about any of the following: 5, 4.9, 4.8, 4.7, 4.6, 4.5, 4.4, 4.3, 4.2, 4.1, and 4 as determined by SS-EN ISO 12945-2, and/or at least about any of the following: 3, 3.2, 3.4, 3.5, 3.6, 3.8, and 4 as determined by SS-EN ISO 12945-2.

In accordance with certain embodiments of the invention, the nonwoven fabric may have a first basis weight from about 4 gsm to about 10 gsm, such as at least about any of the following: 4, 5, 6 and 7 gsm, and/or at most about any of the following: 10, 9, 8, and 7 gsm. The nonwoven fabric may comprise at least one spunbond layer, at least one meltblown layer, at least one carded layer, or any combinations thereof. In accordance with certain embodiments of the invention, the nonwoven fabric comprises one or more spunbond layers formed from a plurality of continuous spunbond fibers. In accordance with certain embodiments of the invention, the nonwoven fabric may have a first bonded area from about 1% to about 40%, such as at least about any of the following: 1, 2, 3, 5, 6, 8, 10, 12, 15, 18, 20, 21, and 22%, and/or at most about any of the following: 40, 38, 35, 32, 30, 28, 25, and 22%. The first bonded area, for example, may be defined by a plurality of separate bonded sites, such as thermal bonded sites, ultrasonically bonded sites, or adhesively formed bonded sites. In this regard, the nonwoven fabric may comprise a relatively low basis weight and relatively low bonded area. Despite this combination of features, the nonwoven fabric of the TBSs, in accordance with certain embodiments of the invention, unexpectedly provide an improved level of abrasion resistance (e.g., reduced lint formation during use).

Figure 1B:
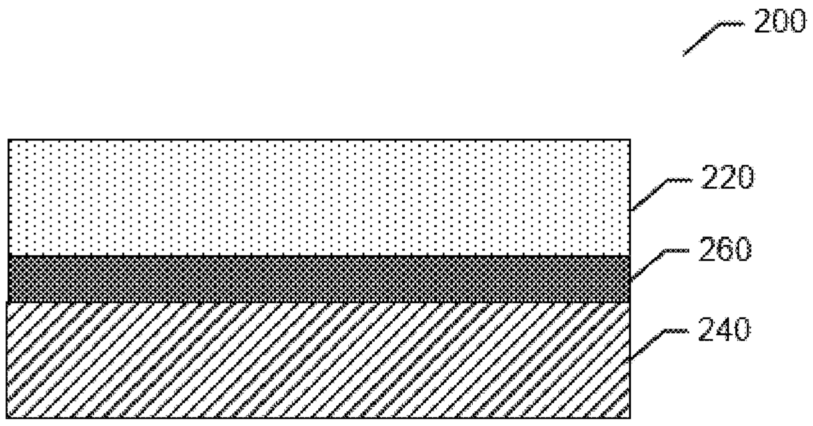
FIG. 1B illustrates a TBS including a nonwoven fabric indirectly bonded to a film, such as a VPLI film or a non-permeable film via an adhesive layer in accordance with certain embodiments of the invention.

FIG. 1A, for instance, illustrates a TBS 100 including a nonwoven fabric 120 directly bonded to a film, such as a VPLI film or a non-permeable 140. In this regard, the nonwoven fabric 120 may, for example, be thermally bonded directly to the film, such as a VPLI film or non-permeable film 140 or the film may be melt-extruded directly onto the nonwoven fabric. FIG. 1B, for instance, illustrates a TBS 200 including a nonwoven fabric 220 indirectly bonded to a film, such as a VPLI film or a non-permeable film 240 via an adhesive layer 260.

In accordance with certain embodiments of the invention, the nonwoven fabric comprises a high-loft nonwoven fabric. The high-loft nonwoven fabric may have a density of less than about 70 kg/m$^3$, such as at most about any of the following: 70, 60, 55, 50, 45, 40, 35, 30, and 25 kg/m3 and/or at least about any of the following: 10, 15, 20, 25, 30, 35, 40, 45, 50, and 55 kg/m$^3$. Additionally or alternatively, the high-loft nonwoven fabric may have a thickness in a z-direction that is perpendicular to a machine-direction and a cross-direction of the nonwoven fabric, in which the thickness comprises from about 0.3 mm to about 3 mm, such as at most about any of the following: 3, 2.75, 2.5, 2.25, 2, 1.75, 1.5, 1.25, 1.0, 0.75, and 0.5 mm and/or at least about any of the following: 0.3, 0.4, 0.5, 0.75, 1.0, 1.25, 1.5, 1.75, and 2.0 mm.

In accordance with certain embodiments of the invention, the nonwoven fabric comprises a first plurality of crimped fibers. The first plurality of crimped fibers may comprise mono-component fibers (e.g., a single polymeric phase or domain) and/or multi-component fibers (e.g., two or more distinct polymeric phases or domains). The first plurality of crimped fibers, for example, may be formed during laydown and/or subsequent to being deposited (e.g., via a thermal and/or mechanical crimping operation that imparts crimped portions to the fibers). In accordance with certain embodiments of the invention, the first plurality of crimped fibers comprise multi-component fibers. The multi-component fibers may comprise continuous fibers, staple fibers, or both. For example, the multi-component fibers may comprise crimped continuous spunbond fibers.

In accordance with certain embodiments of the invention, the first plurality of crimped fibers may comprise self-crimping fibers, in which the crimped portions are formed during the laydown process. In this regard, the multi-component fibers may comprise (i) a first component comprising a first polymeric material having a first melt flow rate (MFR), such as optionally less than 500 g/10 min, less than 400 g/10 min, less than 300 g/10 min, less than 200 g/10 min, less than 100 g/10 min, or less than 50 g/10 min, and (ii) a second component comprising a second polymeric material that is different than the first component, in which the multi-component fibers comprises one or more three-dimensional crimped portions. Optionally the second polymeric material may comprises a second MFR that is, for example, optionally less than 2000 g/10 min, 1500 g/10 min, 1000 g/10 min, 500 g/10 min, less than 400 g/10 min, less than 300 g/10 min, less than 200 g/10 min, less than 100 g/10 min, or less than 50 g/10 min.

The first plurality of crimped fibers may comprise a variety of cross-sectional geometries and/or deniers, such as round or non-round cross-sectional geometries. In accordance with certain embodiments of the invention, first plurality of crimped fibers may comprise all or substantially all of the same cross-sectional geometry or a mixture of differing cross-sectional geometries to tune or control various physical properties. In this regard, the first plurality of crimped fibers may comprise a round cross-section, a non-round cross-section, or combinations thereof. In accordance with certain embodiments of the invention, for example, first plurality of crimped fibers may comprise from about 10% to about 100% of round cross-sectional fibers, such as at most about any of the following: 100, 95, 90, 85, 75, and 50% and/or at least about any of the following: 10, 20, 25, 35, 50, and 75%. Additionally or alternatively, first plurality of crimped fibers may comprise from about 10% to about 100% of non-round cross-sectional fibers, such as at most about any of the following: 100, 95, 90, 85, 75, and 50% and/or at least about any of the following: 10, 20, 25, 35, 50, and 75%. In accordance with embodiments of the invention including non-round cross-sectional crimped fibers, these non-round cross-sectional crimped fibers may comprise an aspect ratio of greater than 1.5:1, such as at most about any of the following: 10:1, 9:1, 8:1, 7:1, 6:1, 5:1, 4:1, 3:1, and 2:1 and/or at least about any of the following: 1.5:1, 2:1, 2.5:1, 3:1, 4:1, 5:1, and 6:1. In accordance with embodiments of the invention including round cross-sectional crimped fibers, these round cross-sectional crimped fibers may comprise an aspect ratio from about 0.8:1 to about 1.2:1. In accordance with certain embodiments of the invention, the aspect ratio, as used herein, may comprise a ratio of the length of the major axis to the length of the minor axis of the cross-section of the fiber in question. In accordance with certain embodiments of the invention, first plurality of crimped fibers may be admixed or blended with non-crimped fibers (e.g., mono-component and/or multi-component fibers) in a single layer of a nonwoven web.

In accordance with certain embodiments of the invention, the first plurality of crimped fibers may comprise a sheath/core configuration, a side-by-side configuration, a pie configuration, an islands-in-the-sea configuration, a multi-lobed configuration, or any combinations thereof. In accordance with certain embodiments of the invention, the sheath/core configuration may comprise an eccentric sheath/core configuration (e.g., bi-component fiber) including a sheath component and core component that is not concentrically located within the sheath component. The core component, for example, may define at least a portion of an outer surface of the crimped fiber having the eccentric sheath/core configuration in accordance with certain embodiments of the invention.

Figure 2A:
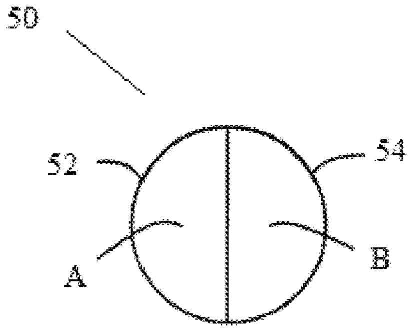
FIG. 2A-2H illustrate examples of cross-sectional views for some example multi-component fibers in accordance with certain embodiments of the invention.
Figure 2B:
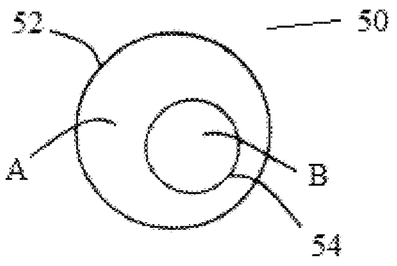
Figure 2C:
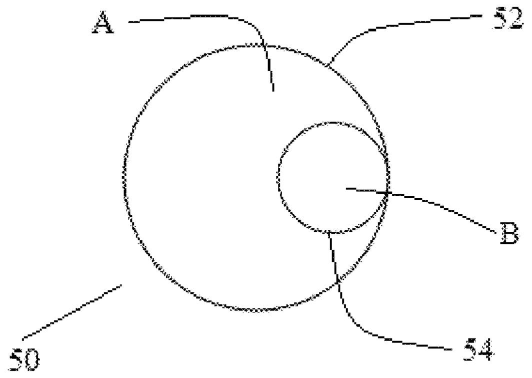
Figure 2D:
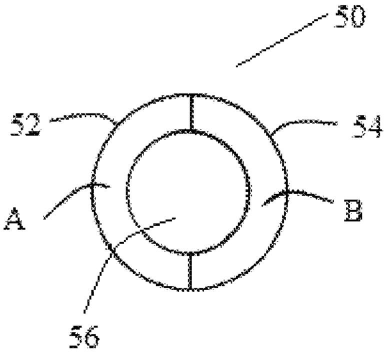
Figure 2E:
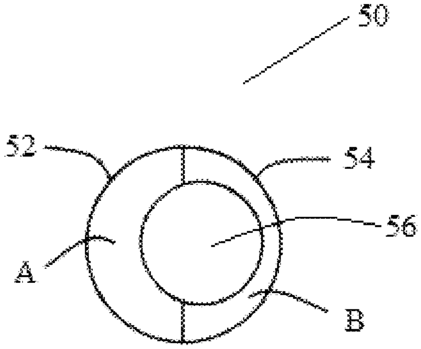
Figure 2F:
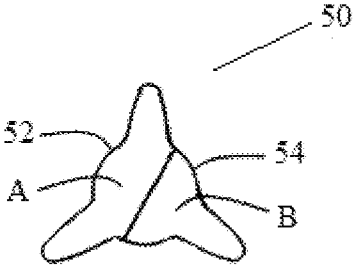
Figure 2G:
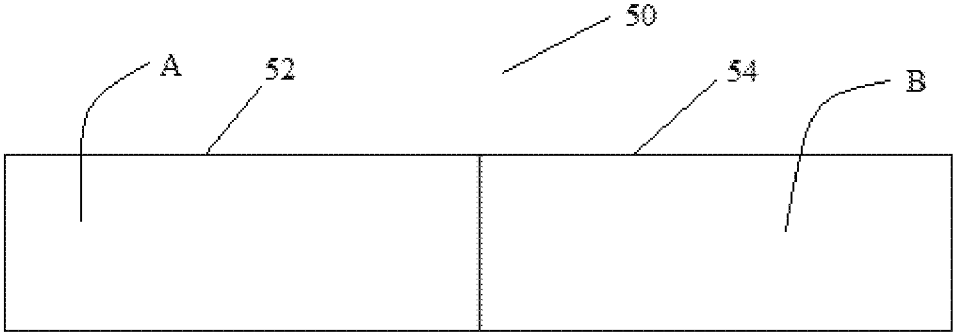
Figure 2H:
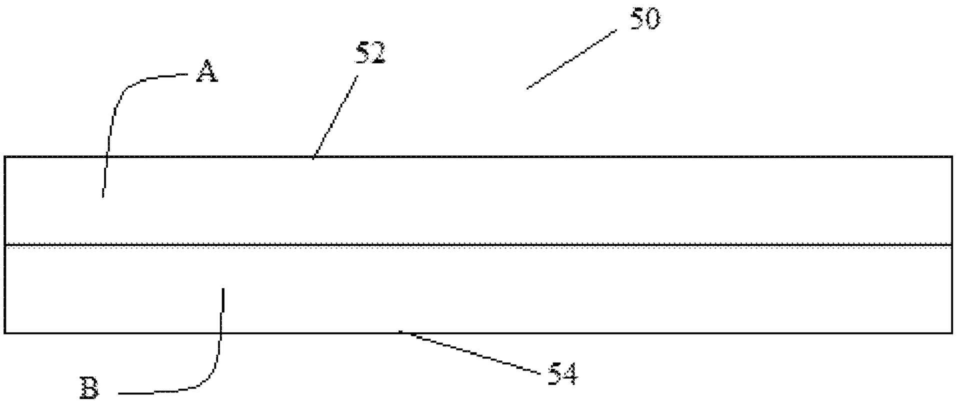

FIGS. 2A-2H illustrate examples of cross-sectional views for some non-limiting examples of the first plurality of crimped fibers in accordance with certain embodiments of the invention. As illustrated in FIG. 2A-2H, the crimped fiber 50 may comprise a first polymeric component 52 of a first polymeric composition A and a second polymeric component 54 of a second polymeric composition B. The first and second components 52 and 54 can be arranged in substantially distinct zones within the cross-section of the crimped fiber that extend substantially continuously along the length of the crimped fiber. The first and second components 52 and 54 can be arranged in a side-by-side arrangement in a round cross-sectional fiber as depicted in FIG. 2A or in a ribbon-shaped (e.g., non-round) cross-sectional fiber as depicted in FIGS. 2G and 2H. Additionally or alternatively, the first and second components 52 and 54 can be arranged in a sheath/core arrangement, such as an eccentric sheath/core arrangement as depicted in FIGS. 2B and 2C. In the eccentric sheath/core crimped fibers as illustrated in FIG. 2B, one component fully occludes or surrounds the other but is asymmetrically located in the crimped fiber to allow fiber crimp (e.g., first component 52 surrounds component 54). Eccentric sheath/core configurations as illustrated by FIG. 2C include the first component 52 (e.g., the sheath component) substantially surrounding the second component 54 (e.g., the core component) but not completely as a portion of the second component may be exposed and form part of the outermost surface of the fiber 50. As additional examples, the crimped fibers can comprise hollow fibers as shown in FIGS. 2D and 2E or as multilobal fibers as shown in FIG. 2F. It should be noted, however, that numerous other cross-sectional configurations and/or fiber shapes may be suitable in accordance with certain embodiments of the invention. In the multi-component fibers, in accordance with certain embodiments of the invention, the respective polymer components can be present in ratios (by volume or by mass) of from about 85:15 to about 15:85. Ratios of approximately 50:50 (by volume or mass) may be desirable in accordance with certain embodiments of the invention; however, the particular ratios employed can vary as desired, such as at most about any of the following: 85:15, 80:20, 75:25, 70:30, 65:35, 60:40, 55:45 and 50:50 by volume or mass and/or at least about any of the following: 50:50, 45:55, 40:60, 35:65, 30:70, 25:75, 20:80, and 15:85 by volume or mass.

As noted above, the first plurality of crimped fibers may comprise a first component comprising a first polymeric composition and a second component comprising a second polymeric composition, in which the first polymeric composition is different than the second polymeric composition. For example, the first polymeric composition may comprise a first polyolefin composition and the second polymeric composition may comprise a second polyolefin composition, a polyester, or a polyamide. In accordance with certain embodiments of the invention, the first polyolefin composition may comprise a first polypropylene or blend of polypropylenes and the second polyolefin composition may comprise a second polypropylene and/or a second polyethylene, in which the first polyolefin composition has, for example, a first melt flow rate and the second polymeric composition (e.g., a second polyolefin composition) has a second melt flow rate, in which the first melt flow rate is different than the second melt flow rate. Additionally or alternatively, the first polypropylene or blend of polypropylenes may have a lower degree of crystallinity than the second polymeric composition (e.g., a second polyolefin composition). In accordance with certain embodiments of the invention, the second polymeric composition, may comprise a polyester, a polyamide, or a bio-polymer (e.g., polylactic acid).

In accordance with certain embodiments of the invention, the first polymeric composition and the second polymeric composition can be selected so that the multi-component fibers develop one or more crimps therein without additional application of heat either in the diffuser section just after the draw unit but before laydown, once the draw force is relaxed, and/or post-treatments such as after fiber lay down and web formation. The polymeric compositions, therefore, may comprise polymers that are different from one another in that they have disparate stress or elastic recovery properties, crystallization rates, and/or melt viscosities. In accordance with certain embodiments of the invention, the polymeric compositions may be selected to self-crimp (e.g., a post-crimping operation may not be necessary after the laydown of the fibers from a spinneret) by virtue of the melt flow rates of the first and second polymeric compositions as described and disclosed herein. In accordance with certain embodiments of the invention, multi-component fibers, for example, can form or have crimped fiber portions having a helically-shaped crimp in a single continuous direction. For example, one polymeric composition may be substantially and continuously located on the inside of the helix formed by the crimped nature of the fiber.

In accordance with certain embodiments of the invention, the first plurality of crimped fibers may include (i) a first group of multi-component fibers having a first identifying feature, such as a first cross-sectional geometry, a first chemical construction, or a first crimp percentage per given length of fiber, and (ii) a second group of multi-component fibers having a second identifying feature, such as a second cross-sectional geometry, a second chemical construction, or a second crimp percentage per given length of fiber, in which the first identifying feature is different than the second identifying feature. The first group of multi-component fibers, for example, may include a polyolefin as at least a portion thereof (e.g., a component of a multi-component fiber), and the second group of multi-component fibers may include a different polyolefin composition or a non-polyolefin as at least a portion thereof.

In accordance with certain embodiments of the invention, the nonwoven fabric may further comprise a plurality of non-crimped fibers. The plurality of non-crimped fibers, for example, may comprise spunbond fibers, meltblown fibers, staple fibers, or any combination thereof. The plurality on non-crimped fibers, for example, may be provided as a separate layer from the first plurality of crimped fibers or intermingled together (e.g., blended and/or physically entangled with each other).

In accordance with certain embodiments of the invention, the film, such as a VPLI film or a non-permeable film may comprise a thickness (e.g., a total thickness) from about 2 to about 200 microns, such as at least about any of the following: 2, 4, 6, 8, 10, 20, 30, 40, 50, 60, 80, and 100 microns, and/or at most about any of the following: 200, 180, 160, 150, 140, 120, and 100 microns. Additionally or alternatively, the film, such as a VPLI film or a non-permeable film may comprise a second basis weight (e.g., a total basis weight) from about 3 to about 16 gsm, such as at least about any of the following: 3, 4, 5, 6, 6.5, 7, 7.5, 8, 8.5, and 9 gsm, and/or at most about any of the following: 16, 15, 14, 13, 12, 11, 10, and 9 gsm. Additionally or alternatively, the film, such as a VPLI film or a non-permeable film may comprise a total density from about 1.0 to about 1.5 g/cm$^3$, such as at least about 1.0, 1.1, 1.2, and 1.25 g/cm$^3$, and/or at most about any of the following: 1.5, 1.4, 1.3, and 1.25 g/cm$^3$. The film, such as a VPLI film or a non-permeable film, in accordance with certain embodiments of the invention, may comprises a single-layer film or a multi-layered film. A multi-layered film, for example, may comprises a core layer located directly or indirectly between two outermost skin layers. In accordance with certain embodiments of the invention, the core layer and the skin layers may be formed from different or identical polymeric compositions. Additionally, a multi-layer film may comprise a plurality of 'A" layers and a plurality of 'B' layers, in which the 'A' layers are formed from a different polymeric composition or melt than the 'B' layers (e.g., polymeric film composition 'A' and polymeric film composition 'B'). In accordance with certain embodiments of the invention, the 'A' layers may define two outermost film layers, wherein the respective 'A' layers and the respective 'B' layers are located in alternating fashion (e.g., AB/AB/AB/A) in which the multi-layer film would include at least one additional 'A' layer relative to the 'B' layers. The multi-layer film, for example, may comprise a total number of individual film layers (e.g., 'A' layers+'B' layers) from 3 to about 32, such as at least about any of the following: 3, 5, 7, 9, 11, 13, 15, 17, and 19 total number of individual film layers, and/or at most about any of the following: 32, 29, 27, 25, 23, 21, and 19 total number of individual film layers. In accordance with certain embodiments of the invention, the multi-layer film may comprise an alternating stack of 'A' layers and 'B' layers, in which a one or more of the respective 'A' layers and/or 'B'layers may define respective 'A' regions and 'B' regions of the multi-layer film (e.g., A/BB/A/BB/A, A/B/AAA/B/A, AA/BB/AA/BB/AA/BB/AA, etc.) In accordance with certain embodiments of the invention, for example, the 'A' layers may comprise microporous film layers and the 'B' layers may comprise monolithic film layers. Alternatively, the 'A' layers and the 'B' layers may all be either monolithic film layers or monolithic film layers. The multi-layer film, for example, can be produced from a multi-fold feedblock.

In accordance with certain embodiments of the invention, the film may comprise a VPLI film comprising a single-layer film that is a monolithic film comprising at least one highly breathable polymer. The highly breathable polymer(s), in accordance with certain embodiments of the invention, may comprise at least one of a thermoplastic urethane (TPU), a polyether block amide copolymer (e.g., PEBAX® from Arkema Group or Vetsamid®E from Evonik), or a copolyester thermoplastic elastomer (e.g., ARNITEL® from DSM Engineering Plastics, HYTREL® from E.I. DuPont de Nemours and Company). The VPLI film, in accordance with certain embodiments of the invention, may comprise a polyether-block-ester copolymer including (i) soft blocks comprising polyethylene glycol and (ii) hard blocks comprising polybutylterephthalate. The VPLI film, in accordance with certain embodiments of the invention, may comprises a copolymer of isotactic polypropylene microcrystalline regions and random amorphous regions. Alternatively or additionally, the VPLI film may comprise a single-layer film that is a microporous film. Microporous films may generally be produced by dispersing finely divided particles of a non-hygroscopic filler material, such as an inorganic salt (e.g., calcium carbonate), into a suitable polymer followed by forming a film of the filled polymer and stretching the film to provide good porosity and water vapor absorption or transmission. In accordance with certain embodiments of the invention, the VPLI film may comprise a polyolefin, such as a polyethylene or a polypropylene, or a copolymer comprising a first polyolefin, such as a first polyethylene, and a second polyolefin, such as a second polypropylene. If a non-permeable film is utilized, the non-permeable film may comprise a polyolefin composition as disclosed herein, but may be substantially devoid of a plurality of micro-pores. In this regard, the non-permeable film prevents and/or inhibits passage of both liquids and vapors (e.g., water vapor).

In accordance with certain embodiments of the invention, the film, such as a VPLI film or a non-permeable film, may comprise a polymeric composition including a polymer component and optional additives (e.g., filler, such as pore-forming filler, UV-stabilizers, surfactants, processing aids, etc.) as a second component. The polymer component, in accordance with certain embodiments of the invention, may comprises a blend of a polypropylene, a polyethylene, and/or optionally a polypropylene-polyethylene copolymer, in which the total ethylene content within the polymer component comprises from about 0 to about 8% by weight, such as at least about any of the following: 0, 0.5, 1, 1.5, 2, 2.5, 3, 3.5, and 4% by weight, and/or at most about any of the following: 8, 7.7, 7, 6.5, 6, 5.5, 5, 4.5, and 4% by weight.

In accordance with certain embodiments of the invention, the film, such as a VPLI film or a non-permeable film, may comprise a multi-layer film, such as those noted above. The multi-layer film may comprise at least a first skin layer and a core layer, wherein the first skin layer has a first thickness and the core layer has a second thickness in which the first thickness is less than the second thickness. The multi-layer film, in accordance with certain embodiments of the invention may comprises a second skin layer, wherein the core layer is located between the first skin layer and the second skin layer. In accordance with certain embodiments of the invention, at least one of the first skin layer and the core layer may comprise a microporous film layer. Additionally or alternatively, the core layer may comprise a monolithic film layer sandwiched between two skin layer, which may be microporous film layers or monolithic film layers. In accordance with certain embodiments of the invention, the core layer and the skin layer(s) may be independently formed from any of the materials described herein. Additionally or alternatively, the core layer may comprise from about 50 to about 95% of the total thickness of the multi-layered film, such as at least about any of the following: 50, 60, 70, and 80% of the total thickness of the multi-layered film, and/or at most about any of the following: 95, 94, 92, 90, 88, 86, 84, 82, and 80% of the total thickness of the multi-layered film. Additionally or alternatively, each of the skin layers may independently from each other comprise from about 2.5 to about 25% of the total thickness of the multi-layered film, such as at least about any of the following: 2.5, 4, 5, 6, 7, 8, 9, and 10% of the total thickness of the multi-layered film, and/or at most about any of the following: 25, 20, 18, 16, 14, 12, and 10% of the total thickness of the multi-layered film.

In accordance with certain embodiments of the invention, the multi-layer film may comprise a plurality of 'A" layers and a plurality of 'B' layers, in which the 'A' layers are formed from a different polymeric composition or melt than the 'B' layers (e.g., polymeric film composition 'A' and polymeric film composition 'B'). The respective 'A' layers and respective 'B' layers may be independently formed from any polymeric composition described herein (e.g., a polymer component and optional additives as a second component). In accordance with certain embodiments of the invention, the 'A' layers may define two outermost film layers, wherein the respective 'A' layers and the respective 'B' layers are located in alternating fashion (e.g., AB/AB/AB/A) in which the multi-layer film would include at least one additional 'A' layer relative to the 'B' layers. The multi-layer film, for example, may comprise a total number of individual film layers (e.g., 'A' layers+'B' layers) from 3 to about 32, such as at least about any of the following: 3, 5, 7, 9, 11, 13, 15, 17, and 19 total number of individual film layers, and/or at most about any of the following: 32, 29, 27, 25, 23, 21, and 19 total number of individual film layers. In accordance with certain embodiments of the invention, the multi-layer film may comprise an alternating stack of 'A' layers and 'B' layers, in which a one or more of the respective 'A' layers and/or 'B' layers may define respective 'A' regions and 'B' regions of the multi-layer film (e.g., A/BB/A/BB/A, A/B/AAA/B/A, AA/BB/AA/BB/AA/BB/AA, etc.) In accordance with certain embodiments of the invention, for example, the 'A' layers may comprise microporous film layers and the 'B' layers may comprise monolithic film layers. Alternatively, the 'A' layers and the 'B' layers may all be either monolithic film layers or monolithic film layers. The multi-layer film, for example, can be produced from a multi-fold feedblock (e.g., devoid of adhesive between each individual respective 'A' and 'B' layers). In accordance with certain embodiments of the invention, an aggregate thickness of the total number of 'A' layers may account or define about 20 to about 95% of the total thickness of the multi-layered film, such as at least about any of the following: 20, 30, 40, and 50% of the total thickness of the multi-layered film, and/or at most about any of the following: 95, 90, 80, 70, 60, and 50% of the total thickness of the multi-layered film. In accordance with certain embodiments of the invention, an aggregate thickness of the total number of 'B' layers may account or define about 20 to about 95% of the total thickness of the multi-layered film, such as at least about any of the following: 20, 30, 40, and 50% of the total thickness of the multi-layered film, and/or at most about any of the following: 95, 90, 80, 70, 60, and 50% of the total thickness of the multi-layered film.

In accordance with certain embodiments of the invention, the VPLI film may have a moisture vapor transmission rate (MVTR) comprising at least about 4000 $g/m^2/24$ hr as determined according to by NWSP 070.4.RO, such as at least about any of the following: 4000, 4500, 5000, 5500, 6000, 6500, 7000, 7500, and 8000 $g/m^2/24$ hr as determined according to by NWSP 070.4.RO, and/or at most about any of the following: 12000, 11000, 10000, 9000, and 8000 $g/m^2/24$ hr as determined according to by NWSP 070.4.RO. In accordance with certain embodiments of the invention, the TBS may have a MVTR comprising at least about 4000 $g/m^2/24$ hr as determined according to by NWSP 070.4.RO, such as at least about any of the following: 4000, 4500, 5000, 5500, 6000, 6500, 7000, 7500, and 8000 $g/m^2/24$ hr as determined according to by NWSP 070.4.RO, and/or at most about any of the following: 12000, 11000, 10000, 9000, and 8000 $g/m^2/24$ hr as determined according to by NWSP 070.4.RO.

In accordance with certain embodiments of the invention, the film, such as a VPLI film or a non-permeable film, may be thermally bonded directly to the nonwoven fabric, such as by a plurality of individual bond sites that directly fuse adjacent portions of the nonwoven fabric to the film. Additionally or alternatively, the film may be melt-extruded directly onto the nonwoven fabric.

Alternatively, the film, such as a VPLI film or a non-permeable film, may be indirectly bonded to the nonwoven fabric via an adhesive layer located between the film and the nonwoven fabric. In this regard, the TBS may comprise an adhesive layer located between and adhering the nonwoven fabric to the film. In accordance with certain embodiments of the invention, the adhesive layer may have a basis weight from about 0.2 to about 5 gsm, such as at least about any of the following: 0.2, 0.4. 0.5, 0.6, 0.8, 1, 1.2. 1.4. 1.5, 1.6, 1.8, 2, 2.2, 2.4, and 2.5 gsm, and/or at most about any of the following: 5, 4, 5, 4, 3.5, 3, and 2.5 gsm. In accordance with certain embodiments of the invention, the adhesive layer may comprise a discontinuous layer including a plurality of individual adhesive deposition locations. Additionally or alternatively, the adhesive layer comprises one or more continuous streaks, one or more discontinuous streaks, or a combination thereof. For example, the adhesive layer comprises one or more continuous streaks that do not overlap in accordance with certain embodiments. Additionally or alternatively, the adhesive layer may comprise one or more continuous streaks, in which a first plurality of continuous streaks define intersection regions defined by overlapping portions of the first plurality of continuous streaks. Alternatively, the adhesive layer comprises a continuous layer.

In accordance with certain embodiments of the invention, the TBS has a hydrohead from about 80 to about 200 mbar determined per EN 20811, such as at least about any of the following: 80, 90, 100, 100, 110, 120, 130, and 140 mbar determined per EN 20811, and/or at most about any of the following: 200, 190, 180, 170, 160, 150, and 140 mbar determined per EN 20811.

In accordance with certain embodiments of the invention, the TBS has a machine-direction tensile strength (MDTS) a peak from about 15 N/25 mm to about 30 N/25 mm as determined by the ASTM D882, such as at least about any of the following: 15, 16, 17, 18, 19, 20, 21, 22, 23 and 24 N/25 mm as determined by the ASTM D882, and/or at most about any of the following: 30, 29, 28, 27, 26, 25, and 24 N/25 mm as determined by the ASTM D882.

In accordance with certain embodiments of the invention, the TBS has a first ratio between the MDTS at peak (N/25 mm per ASTM D882) and the basis weight of the TBS (gsm) from about 1:1 to about 1.5:1, such as at least about any of the following: 1:1, 1.1:1, 1.2:1, and 1.25:1, and/or at most about any of the following: 1.5:1, 1.4:1, 1.3:1, and 1.25:1.

In accordance with certain embodiments of the invention, the TBS has a machine-direction percent elongation at peak from about 40% to about 100% as determined by the ASTM D882, such as at least about any of the following: 40, 45, 50, 52, 54, 55, 56, 58, 60, 62, 64, 65, 66, 68, and 70% as determined by ASTM D882, and/or at most about any of the following: 100, 90, 80, and 70% as determined by ASTM D882.

In accordance with certain embodiments of the invention, the TBS has an average tensile strength (ATS) at peak according to the Formula 1

$$[\text{MDTS at peak (N/25 mm)}+\text{CDTS at peak (N/25 mm)}]/2 \quad \text{[Formula 1]}$$

of from about 12 to about 25 N/25 mm as determined by the ASTM D5035, such as at least about any of the following: 12, 14, 15, 16, 18, and 20 N/25 mm as determined by ASTM D882, and/or at most about any of the following: 25, 24, 22, and 20 N/25 mm as determined by ASTM D882.

In accordance with certain embodiments of the invention, the TBS has a second ratio between the ATS at peak (N/25 mm per ASTM D882) and the basis weight (gsm) of the TBS from at least about any of the following: 0.7, 0.75, 0.8, 0.9, 0.95, and 1, and/or at most about any of the following: 1.4, 1.3, 1.2, 1.1, and 1. Additionally or alternatively, the TBS has a second ratio between the ATS at peak (N/25 mm per ASTM D882) and the basis weight (gsm) of the nonwoven fabric from at least about any of the following: 1.5, 1.6, 1.8, 1.9, and 2, and/or at most about any of the following: 3, 2.8, 2.6, 2.5, 2.4, 2.3, 2.2, 2.1, and 2.

In another aspect, the present invention provides an absorbent article (e.g., a diaper) including a TBS, such as a TBS disclosed herein. In accordance with certain embodiments of the invention, the absorbent article comprises a TBS, such as a TBS disclosed herein, a liquid permeable topsheet, and an absorbent body located between the TBS and the liquid permeable topsheet. In accordance with certain embodiments of the invention, the film, such as a VPLI film or a non-permeable film of the TBS, may be directly or indirectly located between the absorbent body and the nonwoven fabric of the TBS. In accordance with certain embodiments of the invention, the TBSs may be particularly suitable for use in a variety of hygiene-related articles. Non-limiting examples of hygiene-related articles comprising a TBS in accordance with certain embodiment of the invention include femcare pads (e.g., absorbent pads), absorbent liners (e.g., panty liners), baby diapers, adult diapers, pull-ups (e.g., training pants for toddlers).

In yet another aspect, the present invention provide a method of forming a TBS, such as a TBS disclosed herein. The method may comprise providing or forming a nonwoven fabric, providing for forming a film, such as a VPLI film or a non-permeable film, and directly or indirectly bonding the nonwoven fabric to the film. In accordance with certain embodiments of the invention, the step of directly or indirectly bonding the nonwoven fabric to the film comprises directly bonding the nonwoven fabric to the film via the formation of one or more thermal bonds between the nonwoven fabric and the film, via melt-extruding a precursor film directly onto the nonwoven fabric followed by incrementally stretching the precursor film to form the film, or via melt-extruding the film (e.g., a monolithic film or non-permeable film) directly onto the nonwoven fabric. Alternatively, the step of directly or indirectly bonding the nonwoven fabric to the film comprises indirectly bonding the nonwoven fabric to the film via addition of an adhesive layer between the nonwoven fabric and the film. In accordance with certain embodiments of the invention, the adhesive layer may comprise a discontinuous layer including a plurality of individual adhesive deposition locations. Additionally or alternatively, the adhesive layer comprises one or more continuous streaks, one or more discontinuous streaks, or a combination thereof. For example, the adhesive layer comprises one or more continuous streaks that do not overlap in accordance with certain embodiments. Additionally or alternatively, the adhesive layer may comprise one or more continuous streaks, in which a first plurality of continuous streaks define intersection regions defined by overlapping portions of the first plurality of continuous streaks. Alternatively, the adhesive layer comprises a continuous layer.

EXAMPLES

The present disclosure is further illustrated by the following examples, which in no way should be construed as being limiting. That is, the specific features described in the following examples are merely illustrative and not limiting.

Comparative Example

A commercially available textile backsheet identified under the name Sof-flex Ultra N23H, which is available from Berry EU, was utilized as a Comparative Example. In particular, the Comparative Example consists of a 10 gsm film adhered to a 12 gsm nonwoven fabric via a 1 gsm layer of adhesive. As such, the Comparative Example had a total basis weight of 23 gsm.

Example 1

Example 1 consisted of a TBS formed from a 12 gsm nonwoven fabric (e.g., side-by-side continuous fibers having a first component of a first polypropylene and a second component formed from a second polypropylene) adhered to a 8 gsm polyethylene film via a 0.85 gsm adhesive layer. As such, Example 1 had a total basis weight of 20.85 gsm.

Example 2

Example 2 consisted of a TBS formed from a 8 gsm nonwoven fabric (e.g., side-by-side continuous fibers having a first component of a first polypropylene and a second component formed from a second polypropylene) adhered to a 8 gsm polyethylene film via a 0.85 gsm adhesive layer. As such, Example 1 had a total basis weight of 16.85 gsm.

Example 3

Example 3 consisted of a TBS formed from a 6 gsm nonwoven fabric (e.g., side-by-side continuous fibers having a first component of a first polypropylene and a second component formed from a second polypropylene) adhered to a 8 gsm polyethylene film via a 0.85 gsm adhesive layer. As such, Example 1 had a total basis weight of 14.85 gsm.

For sake of clarity, the basic structures of the nonwoven fabrics and films for the Comparative Example, Example 1, Example 2, and Example 3 were nearly identical with the exception of the noted basis weights.

Each of the examples (i.e., Comparative Example, Example 1, Example 2, and Example 3) were subjected to a variety of tests to evaluate physical properties of each TBS. Table 1 provides a summary of these results.

TABLE 1

| Physical Property (units) Test Method | Comparative Example | Example 1 | Example 2 | Example 3 |
|---|---|---|---|---|
| Basis Weight (gsm) ASTM D 3776 | 23 | 20.85 | 16.85 | 14.85 |
| Hydrohead (mbar) EN 20811 | 126.1 | 137.4 | 100.4 | 92.0 |
| MD Tensile Strength @ Peak (N/25 mm) ASTM D882 | 19.4 | 26.9 | 21.9 | 21.1 |
| MD Elongation @ Peak (%) ASTM D882 | 47.1 | 63.4 | 52.8 | 47.6 |
| MD Tensile Strength @ 5% Elongation (N/25 mm) ASTM D882 | 7.8 | 7.6 | 7.4 | 7.2 |
| MD Tensile Strength @ 10% Elongation (N/25 mm) ASTM D882 | 11.9 | 12.2 | 11.9 | 12.2 |
| MD Tensile Strength @ 25% Elongation (N/25 mm) ASTM D882 | 16.7 | 18.5 | 17.1 | 17.5 |
| CD Tensile Strength @ Peak (N/25 mm) | 8.2 | 12.1 | 7.0 | 5.7 |

TABLE 1-continued

| Physical Property (units) Test Method | Comparative Example | Example 1 | Example 2 | Example 3 |
|---|---|---|---|---|
| ASTM D882 | | | | |
| CD Elongation @ Peak (%) | 55.2 | 108.3 | 128.9 | 174.0 |
| ASTM D882 | | | | |
| CD Tensile Strength @ 5% Elongation (N/25 mm) | 2.4 | 1.5 | 1.3 | 1.5 |
| ASTM D882 | | | | |
| CD Tensile Strength @ 10% Elongation (N/25 mm) | 3.8 | 2.2 | 1.7 | 1.9 |
| ASTM D882 | | | | |
| CD Tensile Strength @ 25% Elongation (N/25 mm) | 6.0 | 4.3 | 2.2 | 2.2 |
| ASTM D882 | | | | |
| MVTR ($g/m^2/24$ h) | 7527 | 9360 | 9569 | 8952 |
| NWSP 070.4.R0 | | | | |
| Linting F2 Grade (Abrasion Resistance Grade from 0-5, with 5 being best) | 4.4 | 4.3 | 4.7 | 4.6 |
| SS-EN ISO 12945-2 | | | | |

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

The invention claimed is:

1. A textile backsheet (TBS), comprising:

(i) a nonwoven fabric, wherein the nonwoven fabric has a basis weight from about 4 to about 8 grams-per-square-meter (gsm); and (ii) a microporous vapor-permeable and liquid impermeable (VPLI) film, wherein the microporous VPLI film has a total basis weight from about 3 to about 10 gsm, and wherein the nonwoven fabric is directly or indirectly bonded to the microporous VPLI film;

wherein the TBS has (a) a basis weight from about 10 to about 18 gsm, and (b) an abrasion resistance grade ("Grade") of at least about 3.0 as determined by SS-EN ISO 12945-2; and wherein the microporous VPLI film has a MVTR comprising at least about 4000 $g/m^2/24$ hr as determined according to NWSP 070.4.R0, the TBS has a MVTR comprising at least about 4000 $g/m^2/24$ hr as determined according to NWSP 070.4.R0, or both.

2. The TBS of claim 1, wherein the nonwoven fabric has a first basis weight from about 4 gsm to about 6 gsm.

3. The TBS of claim 1, wherein the nonwoven fabric comprises at least one spunbond layer, at least one meltblown layer, at least one carded layer, or any combinations thereof.

4. The TBS of claim 3, wherein the nonwoven fabric comprises one or more spunbond layers.

5. The TBS of claim 1, wherein the microporous VPLI film comprises a thickness from about 2 to about 8 microns.

6. The TBS of claim 5, wherein the microporous VPLI film comprises a single-layer film.

7. The TBS of claim 5, wherein the microporous VPLI film comprises at least one of a thermoplastic urethane, a polyether-block-amide copolymer, a polyether-block-ester copolymer, polyester-block-amide copolymer, or a copolyester thermoplastic elastomer.

8. The TBS of claim 5, wherein the microporous VPLI film comprises a multi-layer film comprising at least a first skin layer and a core layer, wherein the first skin layer has a first thickness and the core layer has a second thickness, and the first thickness is less than the second thickness.

9. The TBS of claim 1, wherein the TBS has a first ratio between a machine direction tensile strength (MDTS) at peak (N/25 mm) and a basis weight of the TBS (gsm) from about 1:1 to about 1.5:1.

10. The TBS of claim 1, wherein the TBS has a machine-direction percent elongation at peak from about 40% to about 100% as determined by the ASTM D5035.

11. The TBS of claim 1, wherein the film has a basis weight from 3 to 7 gsm.

12. The TBS of claim 1, wherein the film comprises a multi-layer film having from 2 to 9 individual film layers.

13. The TBS of claim 12, wherein the multi-layer film has from 3 to 7 individual film layers.

14. The TBS of claim 1, wherein the nonwoven fabric comprises one or more spunbond layers comprising bi-component fibers.

15. The TBS of claim 1, wherein the nonwoven fabric comprises one or more spunbond layers and one or more meltblown layers.

16. The TBS of claim 1, wherein the TBS has a hydrohead from 80 to 200 mbar determined per EN 20811.

17. The TBS of claim 1, wherein the microporous VPLI film comprises a multi-layer film wherein each individual layer is formed from an identical polymeric composition.

18. The TBS of claim 1, wherein the microporous VPLI film comprises a multi-layer microporous VPLI film, and wherein each individual layer of the multi-layer microporous VPLI film is formed from an identical polymeric composition.

19. The TBS of claim 1, further comprising an adhesive layer positioned between and adjacent each of the nonwoven fabric and the microporous VPLI film, wherein the nonwoven fabric is directly bonded to the microporous VPLI film via the adhesive layer.

20. An absorbent article, comprising:

(i) a TBS according to claim 1;

(ii) a liquid permeable topsheet; and (iii) an absorbent body located between the TBS and the liquid permeable topsheet.

21. The absorbent article of claim 20, wherein the absorbent article comprises a diaper.

22. A method of forming a textile backsheet (TBS), comprising:

(i) providing or forming a nonwoven fabric, wherein the nonwoven fabric has a basis weight from 4 to 8 grams-per-square-meter (gsm);

(ii) providing for forming a film having a total basis weight from 3 to 10 gsm, wherein the film comprises a microporous vapor-permeable and liquid impermeable (VPLI) film; and (iii) directly or indirectly bonding the nonwoven fabric to the film to form the TBS;

wherein the TBS has (a) a basis weight from about 10 to about 18 gsm, and (b) an abrasion resistance grade ("Grade") of at least about 3.0 as determined by SS-EN ISO 12945-2; and wherein the microporous VPLI film has a MVTR comprising at least about 4000 $g/m^2/24$ hr as determined according to NWSP 070.4.R0, the TBS has a MVTR comprising at least about 4000 $g/m^2/24$ hr as determined according to NWSP 070.4.R0, or both.

23. The method of claim 22, wherein the step of directly or indirectly bonding the nonwoven fabric to the microporous VPLI film comprises directly bonding the nonwoven fabric to the microporous VPLI film via the formation of one or more thermal bonds between the nonwoven fabric and the microporous VPLI film, or via melt-extruding a precursor film directly onto the nonwoven fabric followed by incrementally stretching the precursor film to form the microporous VPLI film.

24. The method of claim 22, wherein the step of directly or indirectly bonding the nonwoven fabric to the microporous VPLI film comprises indirectly bonding the nonwoven fabric to the microporous VPLI film via addition of an adhesive layer between the nonwoven fabric and the microporous VPLI film.

* * * * *